United States Patent [19]

Duffett et al.

[11] Patent Number: Plant 6,613

[45] Date of Patent: Feb. 21, 1989

[54] CHRYSANTHEMUM PLANT NAMED BOALDI

[75] Inventors: William E. Duffett; Cornelis P. VandenBerg, both of Salinas, Calif.

[73] Assignee: Yoder Brothers, Inc., Barberton, Ohio

[21] Appl. No.: 94,702

[22] Filed: Sep. 9, 1987

[51] Int. Cl.[4] ..... A01H 5/00

[52] U.S. Cl. ..... Plt./77

[58] Field of Search ..... Plt. 77

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Boaldi particularly characterized by its flat capitulum form; decorative capitulum type; white ray floret color; diameter across face of capitulum of up to 11 cm at maturity when grown as a pinched disbudded pot mum; uniform eight week photoperiodic flowering response to short days; medium plant height when grown as a pinched pot mum; recommended both as disbudded and spray pot mum; and spreading and prolific branching pattern.

1 Drawing Sheet

The present invention comprises a new and distinct cultivar of Chrysanthemum, botanically known as *Chrysanthemum morifolium,* Ramat., and referred to by the cultivar name Boaldi.

Boaldi, identified as 81D11023, was originated from a cross made in a controlled breeding program in Salinas, Calif. in 1980.

The female parent of Boaldi was the cultivar identified as Paragon, disclosed in U.S. Plant Pat. No. 3,368. The male parent of Boaldi was the cultivar identified as Surf, disclosed in U.S. Plant Pat. No. 4,585.

Boaldi was discovered and selected as one flowering plant within the progeny of the stated cross by William E. Duffett in December of 1981, in a controlled environment in Salinas, Calif.

The first act of asexual reproduction of Boaldi was accomplished when vegetative cuttings were taken from the initial selection in February of 1982 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Boaldi are firmly fixed and are retained through successive generations of asexual reproduction.

Boaldi has not been observed under all possible environmental conditions. The phenotype may vary significantly with variations in environment such as temperature, light intensity, and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Boaldi, which, in combination, distinguish this Chrysanthemum as a new and distinct cultivar:

1. Flat capitulum form.
2. Decorative capitulum type.
3. Pure white ray floret color.
4. Diameter across face of capitulum up to 11 cm at maturity, when grown as a pinched disbudded pot mum.

5. Uniform eight week photoperiodic flowering response to short days.
6. Medium plant height requiring 0 to 7 long days after pinch prior to short days and 1 application of 2500 ppm B-9 SP to attain a flowered plant height of 25 to 35 cm for year-round flowerings when grown as a pinched pot mum.
7. Recommended both as disbudded and spray pot mum.
8. Spreading and prolific branching pattern.

The accompanying photographic drawings show typical inflorescence and leaf characteristics of Boaldi, with the colors being as nearly true as possible with illustrations of this type. Sheet 1 is a color photograph of Boaldi grown as a pinched spray pot mum. Sheet 2 is a black and white photograph of three views of the inflorescence of Boaldi. Sheet 3 is a black and white photograph showing the upper and under sides of the leaves of Boaldi at three stages of development (mature, intermediate and immature).

Of the commercial cultivars known to the inventors, the most similar in comparison to Boaldi is the male parent Surf. Reference is made to attached Chart A, which compares certain characteristics of Boaldi to the same characteristics of Surf.

Similar traits are color, capitulum form and type, and flowering response. Boaldi has a larger capitulum diameter, a more spreading branching pattern, and exhibits more vigor than Surf. In addition, Boaldi has a better flower form retention, and a more open spray formation when grown as a spray pot in comparison to Surf.

In the following description, color references are made to The Royal Horticultural Society Colour Chart. The pure white ray floret color of Boaldi is not represented in the RHS Colour Chart. The color values were determined on plant material grown in Salinas, Calif. on Mar. 24, 1987.

Classification:

*Botanical: Chrysanthemum morifolium,* Ramat., cv. Boaldi.

*Commercial:* Decorative disbud and spray pot mum.

INFLORESCENCE

A. Capitulum:
*Form.*—Flat.
*Type.*—Decorative.
*Diameter across face.*—Up to 11 cm at maturity when grown as a pinched disbudded pot mum.

B. Corolla of ray florets:
*Color (general tonality from a distance of three meters).*—White.
*Color (upper surface).*—White, with center of flower 155B to 155D.
*Color (under surface).*—White.
*Shape.*—Flat, oblong.

C. Corolla of disc florets:
*Color* (mature): 154B.
*Color (immature)*: 144B.

D. Reproductive organs:
*Androecium.*—Present on disc florets only; scant pollen.
*Gynoecium.*—Present on both ray and disc florets.

PLANT

A. General appearance:
*Height.*—Medium; 25 to 35 cm as a pinched pot mum with 0 to 7 long days after pinch prior to short days and 1 application of 2500 ppm B-9 SP.
*Branching pattern.*—Spreading and prolific.

B. Foliage:
*Color (upper surface).*—147A.
*Color (under surface).*—147B.
*Shape.*—Lobed and serrated.

CHART A

Comparison of Boaldi and Surf

| CULTIVAR | RAY FLORET COLOR | CAPITULUM FORM & TYPE | BRANCHING PATTERN |
|---|---|---|---|
| Boaldi | White | Flat Decorative | Spreading and prolific |
| Surf | White | Flat Decorative | Semi-spreading |

| CULTIVAR | DIAMETER ACROSS FACE OF CAPITULUM | PLANT HEIGHT | FLOWERING RESPONSE PERIOD |
|---|---|---|---|
| Boaldi | Up to 11 cm | Medium | 8 weeks |
| Surf | 65–95 mm | Short | 8 weeks |

COMPARISONS MADE OF PLANTS GROWN IN SALINAS, CALIFORNIA AND IN LEAMINGTON, ONTARIO, CANADA

We claim:

1. A new and distinct Chrysanthemum plant named Boaldi, as described and illustrated, and particularly characterized as to uniqueness by the combined characteristics of flat capitulum form; decorative capitulum type; white ray floret color; diameter across face of capitulum of up to 11 cm at maturity when grown as a pinched disbudded pot mum; uniform eight week photoperiodic flowering response to short days; medium plant height when grown as a pinched pot mum; recommended both as disbudded and spray pot mum; and spreading and prolific branching pattern.

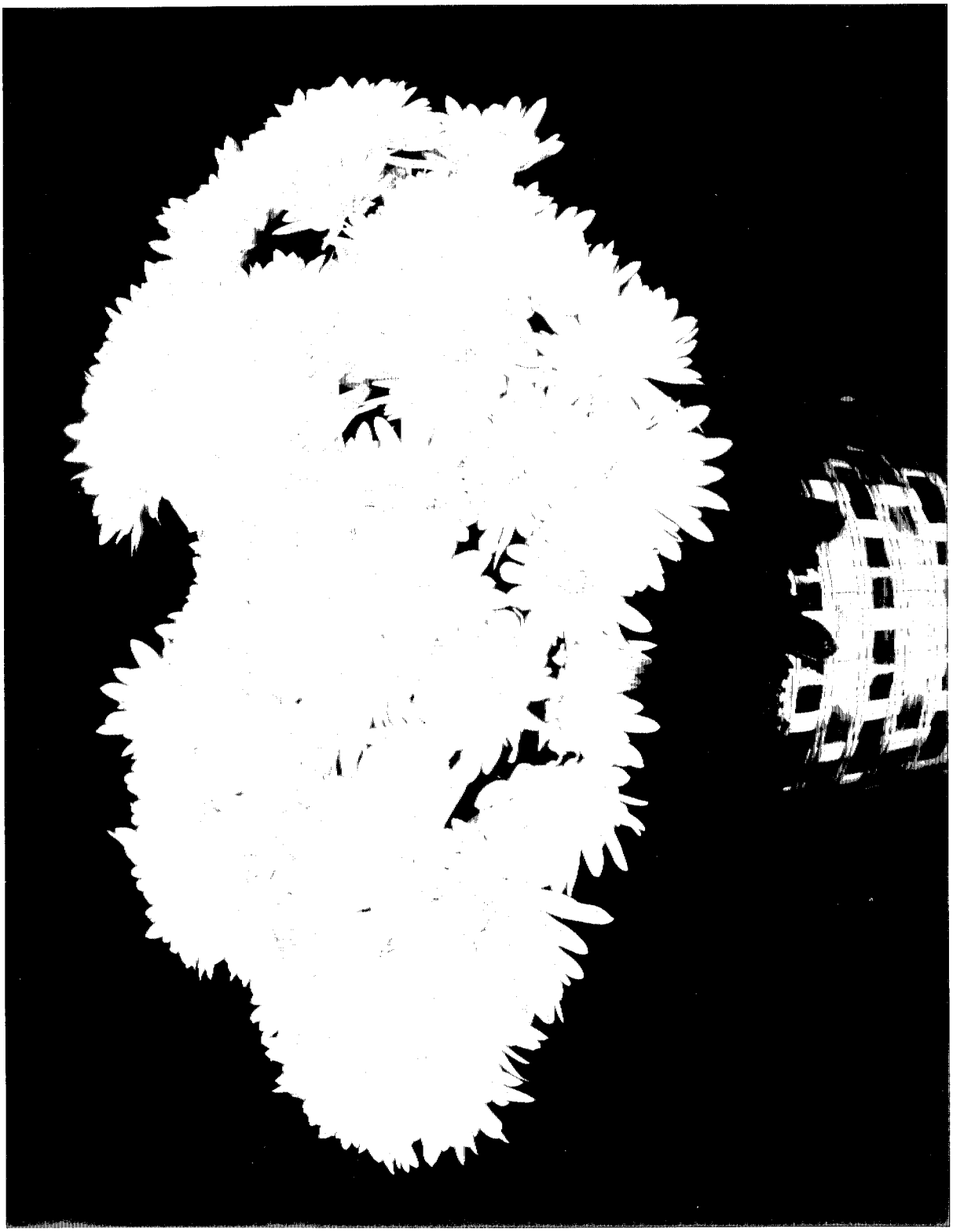

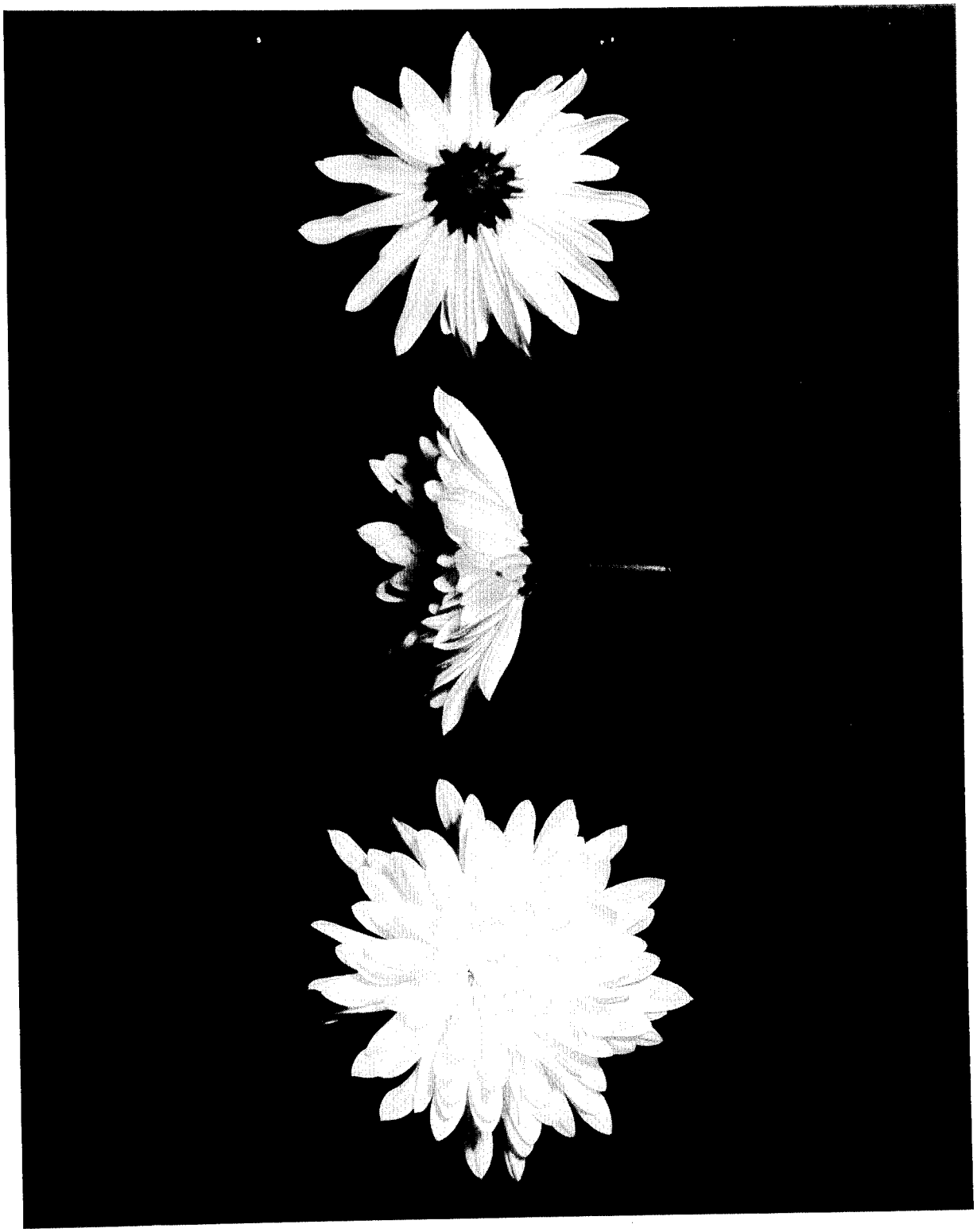

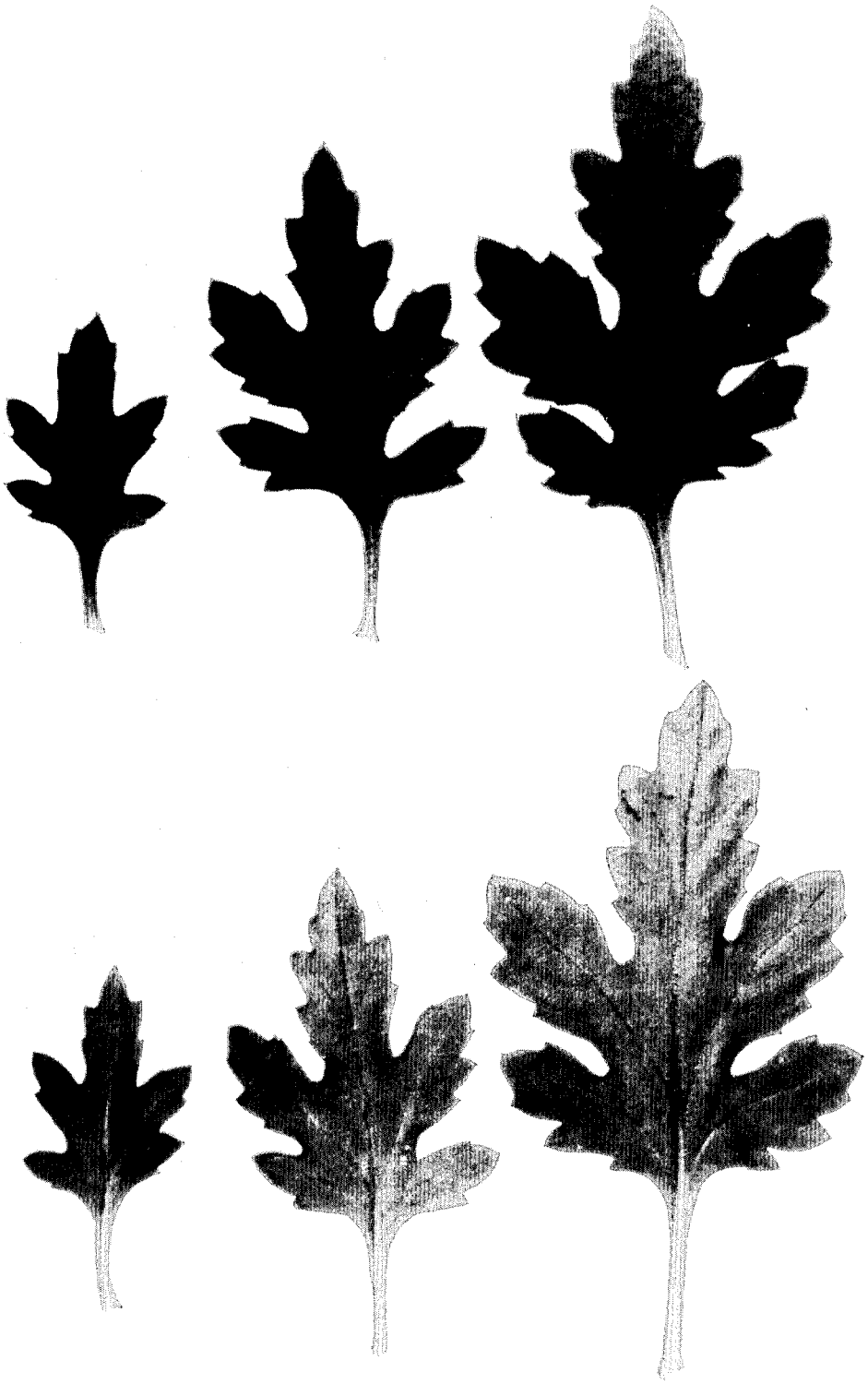

* * * * *